United States Patent
Shimizu

(10) Patent No.: US 10,053,538 B2
(45) Date of Patent: Aug. 21, 2018

(54) METHOD FOR PRODUCING FLUOROPOLYETHER

(71) Applicant: MORESCO CORPORATION, Hyogo (JP)

(72) Inventor: Tsuyoshi Shimizu, Hyogo (JP)

(73) Assignee: MORESCO CORPORATION, Hyogo (JP)

( * ) Notice: Subject to any disclaimer, the term of this patent is extended or adjusted under 35 U.S.C. 154(b) by 0 days.

(21) Appl. No.: 15/525,323

(22) PCT Filed: Jul. 28, 2015

(86) PCT No.: PCT/JP2015/071897
§ 371 (c)(1),
(2) Date: May 9, 2017

(87) PCT Pub. No.: WO2016/092900
PCT Pub. Date: Jun. 16, 2016

(65) Prior Publication Data
US 2017/0321006 A1  Nov. 9, 2017

(30) Foreign Application Priority Data

Dec. 12, 2014 (JP) ................. 2014-251666

(51) Int. Cl.
| | | |
|---|---|---|
| C08G 65/00 | (2006.01) |
| C07C 43/12 | (2006.01) |
| C08G 65/323 | (2006.01) |
| C08G 65/324 | (2006.01) |
| C08G 85/00 | (2006.01) |
| C07C 43/13 | (2006.01) |
| C07C 41/18 | (2006.01) |
| C07C 51/58 | (2006.01) |
| C07C 59/135 | (2006.01) |
| C07B 61/00 | (2006.01) |

(52) U.S. Cl.
CPC ........ *C08G 65/3236* (2013.01); *C07C 43/135* (2013.01); *C08G 65/007* (2013.01); *C08G 65/324* (2013.01); *C08G 85/004* (2013.01); *C08G 2650/02* (2013.01); *C08G 2650/48* (2013.01)

(58) Field of Classification Search
CPC .................................................. C08G 65/00
USPC ....................................................... 528/401
See application file for complete search history.

(56) References Cited

U.S. PATENT DOCUMENTS

| | | |
|---|---|---|
| 4,720,527 A | 1/1988 | Caporiccio et al. |
| 2002/0022752 A1 | 2/2002 | Okazoe et al. |
| 2010/0136371 A1 | 6/2010 | Shimizu et al. |

FOREIGN PATENT DOCUMENTS

| | | |
|---|---|---|
| GB | 1104482 | 2/1968 |
| JP | 1985-202122 | 10/1985 |
| JP | 2005-225816 | 8/2005 |
| JP | 2009-270093 | 11/2009 |
| WO | 02/20445 | 3/2002 |
| WO | 2009/008380 | 1/2009 |

OTHER PUBLICATIONS

International Search Report dated Oct. 6, 2015 in International (PCT) Application No. PCT/JP2015/071897.
Behr et al., "A Lewis acid catalytic process for preparing fluorocarboxylic acid halides", Journal of Fluorine Chemistry, vol. 112, No. 2, 2001, pp. 369-372.

*Primary Examiner* — Duc Truong
(74) *Attorney, Agent, or Firm* — Wenderoth, Lind & Ponack, L.L.P.

(57) ABSTRACT

A process for preparing a low-molecular weight fluoropolyether containing an acid fluoride by decomposing a triflate or trifluoroacetate of a fluoropolyether having a hydroxyl group in the presence of a Lewis acid.

11 Claims, No Drawings

METHOD FOR PRODUCING FLUOROPOLYETHER

TECHNICAL FIELD

The present invention relates to a process for preparing a fluoropolyether by cleavage of a fluoropolyether having a hydroxyl group, the former fluoropolyether being lower than the latter fluoropolyether in molecular weight.

BACKGROUND ART

A fluoropolyether is obtained, for example, by photooxidation of a perfluoroolefin, ring-opening polymerization of a partially fluorinated oxetane compound, fluorination of a hydrogenated polyalkylene compound (Patent Literatures 1 and 2). In these methods, it is generally known that a final product having too much molecular weight is obtained and use thereof is practically restricted. In practice, these high-molecular weight product was applied only to the limited use. Among very interesting applications, there is an application in electric or electronic fields in which a low-molecular weight fluoropolyether is required.

A process is known in which a fluoropolyether having no hydroxyl group is cleaved using a Lewis acid to obtain a low-molecular weight fluoropolyether (Patent Literatures 3).

However, a process is not known in which a fluoropolyether having hydroxyl group is cleaved to obtain a low-molecular weight fluoropolyether, since the fluoropolyether deactivates a Lewis acid.

PATENT LITERATURE

Patent Literature 1: GB 1104482
Patent Literature 2: JP 1985-202122A
Patent Literature 3: U.S. Pat. No. 4,720,527

SUMMARY OF THE INVENTION

Problem to be Solved by the Invention

An object of the present invention is to provide a process for preparing a low-molecular weight fluoropolyether containing an acid fluoride by cleavage of a fluoropolyether having a hydroxyl group.

Means for Solving the Problem of the Invention

The present invention provides the following.

1. A process for preparing a low-molecular weight fluoropolyether containing an acid fluoride by decomposing a triflate or trifluoroacetate of a fluoropolyether having a hydroxyl group in the presence of a Lewis acid.

2. A process as defined in claim 1 wherein the triflate is at least one selected among
A-$(CF_2CF_2O)x(CF_2O)yCF_2CH_2OTf$
TfO$CH_2CF_2O(CF_2CF_2O)x(CF_2O)yCF_2CH_2OTf$
A-$(CF_2CF_2CF_2O)zCF_2CF_2CH_2OTf$
TfO$CH_2CF_2CF_2O(CF_2CF_2CF_2O)zCF_2CF_2CH_2OTf$
A-$(CF_2CF_2CF_2CF_2O)nCF_2CF_2CF_2CH_2OTf$
TfO$CH_2CF_2CF_2CF_2O(CF_2CF_2CF_2CF_2O)$
n$CF_2CF_2CF_2CH_2OTf$,
A is fluoroalkoxy, Tf is $CF_3SO_2$, x, y, z and n are a real number of 1 to 100.

3. A process as defined in claim 1 wherein the trifluoroacetate is at least one selected among
A-$(CF_2CF_2O)x(CF_2O)yCF_2CH_2OTfa$
TfaO$CH_2CF_2O(CF_2CF_2O)x(CF_2O)yCF_2CH_2OTfa$
A-$(CF_2CF_2CF_2O)zCF_2CF_2CH_2OTfa$
TfaO$CH_2CF_2CF_2O(CF_2CF_2CF_2O)zCF_2CF_2CH_2OTfa$
A-$(CF_2CF_2CF_2CF_2O)nCF_2CF_2CF_2CH_2OTfa$
TfaO$CH_2CF_2CF_2CF_2O(CF_2CF_2CF_2CF_2O)$
n$CF_2CF_2CF_2CH_2OTfa$,
A is fluoroalkoxy, Tfa is $CF_3CO$, x, y, z and n are a real number of 1 to 100.

4. A process as defined in claim 1 wherein the acid fluoride is at least one selected among
A-$(CF_2CF_2O)xa(CF_2O)ya$-$CF_2COF$
FOC—$CF_2O(CF_2CF_2O)xa(CF_2O)ya$-$CF_2COF$
A-$(CF_2CF_2CF_2O)za$-$CF_2CF_2COF$
FOC—$CF_2CF_2O(CF_2CF_2CF_2O)za$-$CF_2CF_2COF$
A-$(CF_2CF_2CF_2CF_2O)na$-$CF_2CF_2CF_2COF$
FOC—$CF_2CF_2CF_2O(CF_2CF_2CF_2CF_2O)na$-
$CF_2CF_2CF_2COF$,
A is fluoroalkoxy, $0.1x \leq xa \leq 0.9x$, $0.1y \leq ya \leq 0.9y$, $0.1z \leq za \leq 0.9z$, $0.1n \leq na \leq 0.9n$, x, y, z and n are a real number of 1 to 100.

5. A process as defined in any one of claims 2 to 4 wherein x and y are each a real number of 1 to 30, z is a real number of 1 to 30, n is a real number of 1 to 30.

Effect of the Invention

In the present invention, it is possible to prepare a fluoropolyether having a molecular weight lower than a starting fluoropolyether and containing an acid fluoride by modifying a hydroxyl group of the starting fluoropolyether to a triflate or trifluoroacetate and cleaving the fluoropolyether with heating in the presence of a Lewis acid.

EMBODIMENT OF PRACTICING THE INVENTION

Examples of fluoropolyethers having a hydroxyl group are below.
A-$(CF_2CF_2O)x(CF_2O)yCF_2CH_2OH$
HO$CH_2CF_2O(CF_2CF_2O)x(CF_2O)yCF_2CH_2OH$
A-$(CF_2CF_2CF_2O)zCF_2CF_2CH_2OH$
HO$CH_2CF_2CF_2O(CF_2CF_2CF_2O)zCF_2CF_2CH_2OH$
A-$(CF_2CF_2CF_2CF_2O)nCF_2CF_2CF_2CH_2OH$
HO$CH_2CF_2CF_2CF_2O(CF_2CF_2CF_2CF_2O)$
n$CF_2CF_2CF_2CH_2OH$,
A is fluoroalkoxy, x, y, z and n are a real number of 1 to 100.

Examples of fluoroalkoxy groups of A are fluoroalkoxy groups having 1 to 6, preferably 2 to 4 and more preferably 2 and 3 carbon atoms. Specific examples are $CF_3CF_2CF_2CF_2O$, $CF_3CF_2CF_2O$ and $CF_3CF_2O$.

The above x, y, z and n are each preferably 1 to 70, more preferably 1 to 50 and particularly preferably 1 to 30.

It is possible to prepare a triflate or trifluoroacetate of a fluoropolyether by reacting a trifluoromethanesulfonic anhydride or trifluoroacetic anhydride with a fluoropolyether having a hydroxyl group. The reaction is preferably conducted by using one to three equivalents of trifluoromethanesulfonic anhydride or trifluoroacetic anhydride per equivalent of a hydroxyl group, in the presence of a base, at an atmosphere of an inert gas and at room temperature for 1 to 48 hours with stirring. Examples of bases are pyridine, imidazole and tripropylamine. Examples of inert gas are nitrogen and argon.

Examples of the triflates are
A-$(CF_2CF_2O)x(CF_2O)yCF_2CH_2OTf$,
TfO$CH_2CF_2O(CF_2CF_2O)x(CF_2O)yCF_2CH_2OTf$,
A-$(CF_2CF_2CF_2O)zCF_2CF_2CH_2OTf$, TfOCH$_2$CF$_2$CF$_2$O(CF$_2$CF$_2$CF$_2$O)zCF$_2$CF$_2$CH$_2$OTf,
A-(CF$_2$CF$_2$CF$_2$O)nCF$_2$CF$_2$CF$_2$CH$_2$OTf and
TfOCH$_2$CF$_2$CF$_2$O(CF$_2$CF$_2$CF$_2$O)
nCF$_2$CF$_2$CF$_2$CH$_2$OTf,
A is fluoroalkoxy, Tf is CF$_3$SO$_2$, x, y, z and n are the same as above.

Examples of the trifluoroacetates are
A-(CF$_2$CF$_2$O)x(CF$_2$O)yCF$_2$CH$_2$OTfa,
TfaOCH$_2$CF$_2$O(CF$_2$CF$_2$O)x(CF$_2$O)yCF$_2$CH$_2$OTfa,
A-(CF$_2$CF$_2$CF$_2$O)zCF$_2$CF$_2$CH$_2$OTfa,
TfaOCH$_2$CF$_2$CF$_2$O(CF$_2$CF$_2$CF$_2$O)zCF$_2$CF$_2$CH$_2$OTfa,
A-(CF$_2$CF$_2$CF$_2$CF$_2$O)nCF$_2$CF$_2$CF$_2$CH$_2$OTfa and
TfaOCH$_2$CF$_2$CF$_2$CF$_2$O(CF$_2$CF$_2$CF$_2$CF$_2$O)
nCF$_2$CF$_2$CF$_2$CH$_2$OTfa,
A is fluoroalkoxy, Tfa is CF$_3$CO, x, y, z and n are the same as above.

The resulting triflate or trifluoroacetate of the fluoropolyether is decomposed with heating in the presence of a Lewis acid to prepare a low-molecular weight fluoropolyether containing an acid fluoride. Examples of the Lewis acids are a metal oxide such as aluminum oxide, and a metal halide such as aluminum chloride. The reaction is preferably conducted by using 0.1 to 30% by weight of Lewis acid based on the triflate or trifluoroacetate of the fluoropolyether in an atmosphere of an inert gas and at 150 to 350° C. for 1 to 48 hours with heat and stirring.

Examples of the acid fluoride are
A-(CF$_2$CF$_2$O)xa(CF$_2$O)ya-CF$_2$COF,
FOC—CF$_2$O(CF$_2$CF$_2$O)xa(CF$_2$O)ya-CF$_2$COF,
A-(CF$_2$CF$_2$CF$_2$O)za-CF$_2$CF$_2$COF,
FOC—CF$_2$CF$_2$O(CF$_2$CF$_2$CF$_2$O)za-CF$_2$CF$_2$COF,
A-(CF$_2$CF$_2$CF$_2$CF$_2$O)na-CF$_2$CF$_2$CF$_2$COF and
FOC—CF$_2$CF$_2$CF$_2$O(CF$_2$CF$_2$CF$_2$CF$_2$O)na-CF$_2$CF$_2$CF$_2$COF,
A is fluoroalkoxy, $0.1x \le xa \le 0.9x$, $0.1y \le ya \le 0.9y$, $0.1z \le za \le 0.9z$, $0.1n \le na \le 9n$, x, y, z and n are the same as above.

Preferable are $0.2x \le xa \le 0.8$ x, $0.2y \le ya \le 0.8y$, and $0.2n \le na \le 0.8n$. More preferable are $0.3x \le xa \le 0.6x$, $0.3y \le ya \le 0.6y$, $0.3z \le za \le 0.6$ z, and $0.3n \le na \le 0.6n$.

In the present invention, a fluoropolyether having a molecular weight lower than a starting fluoropolyether is obtained other than the acid fluoride. Examples of the fluoropolyether are
A-(CF$_2$CF$_2$O)xa(CF$_2$O)ya-B,
A-(CF$_2$CF$_2$CF$_2$O)za-B and
A-(CF$_2$CF$_2$CF$_2$CF$_2$O)na-B,
A is fluoroalkoxy, B is fluoroalkyl, xa, ya, za and na are the same as above.

Examples of the fluoroalkoxy A are as above and those having 1 to 6, preferably 2 to 4 and further preferably 2 and 3 carbon atoms. Specific examples are CF$_3$CF$_2$CF$_2$CF$_2$O, CF$_3$CF$_2$CF$_2$O and CF$_3$CF$_2$O.

Examples of the fluoroalkyl B are those having 1 to 6, preferably 2 to 4 and further preferably 2 and 3 carbon atoms. Specific examples are —CF$_2$CF$_2$CF$_2$CF$_3$, —CF$_2$CF$_2$CF$_3$ and —CF$_2$CF$_3$.

By reacting a reducing agent such as NaBH$_4$ or LiAlH$_4$ with the low-molecular weight fluoropolyether containing an acid fluoride of the present invention (hereinafter referred to as "the present compound), the acid fluoride is modified to a hydroxyl compound. Further, this hydroxyl compound can be converted to a phosphazene compound such as Patent Literature 4 or a compound containing an aromatic ring such as Patent Literature 5.

Patent Literature 4: US 2010/136371A
Patent Literature 5: JP 2009270093A

The above hydroxyl compound derived from the acid fluoride, the phosphazene compound such as Patent Literature 4 or the compound containing an aromatic ring such as Patent Literature 5 (hereinafter referred to as "the compound derived from the present compound) can be used for example as a lubricant for a magnetic disk.

The compound derived from the present compound is applied to the magnetic disk surface preferably by diluting the compound with a solvent and coating the disk surface with the diluted compound. Examples of useful solvents are PF-5060, PF-5080, HFE-7100 and HFE-7200 manufactured by 3M, Vertrel-XF, product of DuPont, etc.

While the compound derived from the present compound is usable singly, the compound can be used also as mixed in a desired ratio with another material, such as Fomblin Zdol, Ztetraol, Zdol TX, AM manufactured by Solvay Solexis, Demnum manufactured by Daikin Industries, Ltd., Krytox manufactured by DuPont, or the like.

Examples of the hydroxyl compound derived from the acid fluoride are
A-(CF$_2$CF$_2$O)xa(CF$_2$O)ya-CF$_2$CH$_2$OH,
HO—CH$_2$CF$_2$O(CF$_2$CF$_2$O)xa(CF$_2$O)ya-CF$_2$CH$_2$OH,
A-(CF$_2$CF$_2$CF$_2$O)za-CF$_2$CF$_2$CH$_2$OH,
HO—CH$_2$CF$_2$CF$_2$O(CF$_2$CF$_2$CF$_2$O)za-CF$_2$CF$_2$CH$_2$OH,
A-(CF$_2$CF$_2$CF$_2$CF$_2$O)na-CF$_2$CF$_2$CF$_2$CH$_2$OH and
HO—CH$_2$CF$_2$CF$_2$CF$_2$O(CF$_2$CF$_2$CF$_2$CF$_2$O)na-CF$_2$CF$_2$CF$_2$CH$_2$OH,
A is fluoroalkoxy, $0.1x \le xa \le 0.9x$, $0.1y \le ya \le 0.9y$, $0.1z \le za \le 0.9z$, $0.1n \le na \le 0.9n$, x, y, z and n are the same as above.

The phosphazene compound of Patent Literature 4 is shown by the formula below

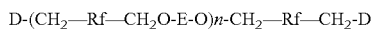

wherein n is an integer of 1 to 4, D is a group of the formula (a), E is a group of the formula (b), p is 1 or 2, R is fluoroalkyl having 1 to 4 carbon atoms, Rf is —CF$_2$O(CF$_2$CF$_2$O) x' (CF$_2$O)y' CF$_2$— or —CF$_2$CF$_2$O(CF$_2$CF$_2$CF$_2$O)z' CF$_2$CF$_2$—, x', y' and z' are each a real number of 0 to 50.

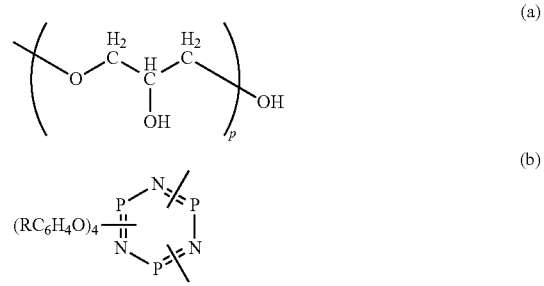

The compound containing an aromatic ring of Patent Literature 5 is shown by the formula below

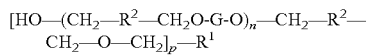

wherein n is an integer of 0 to 6, G is a group of the formula —CH$_2$CH(OH) CH$_2$—, R$^1$ is an aromatic group of C$_6$H$_{6-p}$, C$_6$H$_{5-q}$—O—C$_6$H$_{5-r}$ or C$_{10}$H$_{8-p}$, p is an integer of 3 to 6, q and r are each an integer of at least 0, p=q+r, R$^2$ is —CF$_2$O(CF$_2$CF$_2$O)$_{x''}$(CF$_2$O)$_{y''}$CF$_2$— or —CF$_2$CF$_2$O(CF$_2$CF$_2$CF$_2$O)$_{z''}$CF$_2$CF$_2$—, x" and y" are each a real number of 0 to 30, z" is a real number of 1 to 30.

EXAMPLES

The invention will be described in more detail with reference to the following examples to which, however, the invention is not limited.

Example 1

Preparation of A-$(CF_2CF_2CF_2O)zCF_2CF_2CH_2OTf$ (Compound 1) A=$CF_3CF_2CF_2O$—, Tf=$CF_3SO_2$—

In an argon atmosphere, 100 g of trifluoromethane-sulfonic anhydride was added dropwise for one hour to a mixture of 570 g of dichloromethane, 285 g of a fluoropolyether of the formula $CF_3CF_2CF_2O(CF_2CF_2CF_2O)$ $zCF_2CF_2CH_2OH$ (2004 in number average molecular weight and 1.25 in molecular weight distribution) and 34 g of pyridine. The mixture was stirred at room temperature for 17 hours. The mixture was thereafter washed with water, dewatered and purified by silica gel column chromatography, affording 282 g of Compound 1.

Compound 1 was a colorless transparent liquid and 1.74 g/cm$^3$ in density at 20° C. Compound 1 was identified by NMR with the result shown. Compound 1 was 2158 in number average molecular weight which was obtained by a method for determining terminal group using $^{19}$F-NMR (same as hereinafter).

$^{19}$F-NMR (solvent: none, reference material: $OCF_2C$ $\underline{F}_2CF_2O$ in the obtained product being taken as −129.7 ppm)
δ=−129.7 ppm
[20F, —$OCF_2C\underline{F}_2CF_2O$—]
δ=−83.7 ppm
[40F, —$OC\underline{F}_2CF_2C\underline{F}_2O$—]
δ=−124.7 ppm
[2F, —$OC\underline{F}_2CF_2CH_2OSO_2CF_3$]
δ=−86.8 ppm
[2F, —$OCF_2C\underline{F}_2CH_2OSO_2CF_3$]
δ=−76.0 ppm
[3F, —$OCF_2CF_2CH_2OSO_2C\underline{F}_3$]
δ=−130.7 ppm
[2F, $CF_3C\underline{F}_2CF_2O$—]
δ=−84.7 ppm
[2F, $CF_3CF_2C\underline{F}_2O$—]
δ=−82.4 ppm
[3F, $C\underline{F}_3CF_2CF_2O$—]
z=10.2
$^1$H-NMR (solvent: none, reference material: $D_2O$)
δ=3.2 ppm
[2H, —$OCF_2CF_2C\underline{H}_2OSO_2CF_3$]

Example 2

Preparation of a mixture (Mixture 1) of $CF_3CF_2O$ $(CF_2CF_2CF_2O)_{za}CF_2CF_2COF$ (Compound 2), $FOCCF_2CF_2O(CF_2CF_2CF_2O)_{za}CF_2CF_2COF$ (Compound 3) and $CF_3CF_2CF_2O(CF_2CF_2CF_2O)_{za}CF_2CF_2CF_3$ (Compound 4)

In an argon atmosphere, 57 g of Compound 1 (2158 in number average molecular weight and 1.23 in molecular weight distribution) and 3 g of aluminum chloride were heated for reflux at 250° C. for 2 hours. After cooled to room temperature, solid reaction byproducts were filtered off to obtain 28 g of Mixture 1 of Compound 2, Compound 3 and Compound 4 as a filtrate.

Mixture 1 was a light yellow transparent liquid and 1.69 g/cm$^3$ in density at 20° C. Mixture 1 was identified by NMR with the result shown. Mixture 1 was 1045 in number average molecular weight.

$^{19}$F-NMR (solvent: none, reference material: $OCF_2CF_2C$ $\underline{F}_2O$ in the obtained product being taken as −129.7 ppm)
δ=−129.7 ppm
[9F, —$OCF_2C\underline{F}_2CF_2O$—]
δ=−83.7 ppm
[17F, —$OC\underline{F}_2CF_2C\underline{F}_2O$—]
δ=−86.3 ppm
[2F, —$OC\underline{F}_2CF_3COF$]
δ=−122.1 ppm
[2F, —$OCF_3C\underline{F}_2COF$]
δ=−21.7 ppm
[1F, —$OCF_2CF_3CO\underline{F}$]
δ=−130.7 ppm
[2F, $CF_3C\underline{F}_2CF_2O$—]
δ=−84.7 ppm
[2F, $CF_3CF_2C\underline{F}_2O$—]
δ=−82.4 ppm
[3F, $C\underline{F}_3CF_2CF_2O$—]
za=4.28

Example 3

Preparation of $TfaOCH_2CF_2O(CF_2CF_2O)_x(CF_2O)_y$ $CF_2CH_2OTfa$ (Compound 5)
Tfa=$CF_3CO$—

In an argon atmosphere, 50 g of trifluoroacetic anhydride was added dropwise for one hour to 200 g of a fluoropolyether of the formula $HOCH_2CF_2O(CF_2CF_2O)x(CF_2O)_y$ $CF_2CH_2OH$ (2071 in number average molecular weight and 1.15 in molecular weight distribution). The mixture was stirred at room temperature for 17 hours. Thereafter, low-boiling components were removed by an evaporator, affording 202 g of Compound 5.

Compound 5 was a colorless transparent liquid and 1.69 g/cm$^3$ in density at 20° C. Compound 5 was identified by NMR with the result shown. Compound 5 was 2265 in number average molecular weight.

$^{19}$F-NMR (solvent: none, reference material: $OCF_2C\underline{F}_2C$ $\underline{F}_2CF_2O$ in the obtained product being taken as −125.8 ppm)
δ=−52.1 ppm, −53.7 ppm, −55.4 ppm
[21F, —$OC\underline{F}_2O$—]
δ=−78.7 ppm, −80.6 ppm
[4F, —$C\underline{F}_2CH_2OCOCF_3$]
δ=−76.7 ppm
[6F, —$CF_2CH_2OCOC\underline{F}_3$]
δ=−89.1 ppm, −90.7 ppm
[40F, —$OC\underline{F}_2C\underline{F}_2O$—]
x=10.1, y=10.4
$^1$H-NMR (solvent: none, reference material: $D_2O$)
δ=5.0 ppm
[4H, —$OCF_2C\underline{H}_2OCOCF_3$]

Example 4

Preparation of a mixture (Mixture 2) of $CF_3CF_2O$ $(CF_2CF_2O)_{xa}$ $(CF_2O)_{ya}CF_2CF_2COF$ (Compound 6), $FOCCF_2O(CF_2CF_2O)_{xa}$ $(CF_2O)_{ya}CF_2COF$ (Compound 7) and $CF_3CF_2O(CF_2CF_2O)_{xa}$ $(CF_2O)_{ya}CF_2CF_3$ (Compound 8)

In an argon atmosphere, 60 g of Compound 5 (2265 in number average molecular weight and 1.14 in molecular weight distribution) and 6 g of aluminum oxide were heated for reflux at 250° C. for 2 hours. After cooled to room temperature, solid reaction byproducts were filtered off to obtain 30 g of Mixture 2 of Compound 6, Compound 7 and Compound 8 as a filtrate.

Mixture 2 was a light yellow transparent liquid and 1.70 g/cm$^3$ in density at 20° C. Mixture 2 was identified by NMR with the result shown. Mixture 2 was 968 in number average molecular weight.

$^{19}$F-NMR (solvent: none, reference material: OCF$_2$CF$_2$CF$_2$O in the obtained product being taken as −125.8 ppm)

δ=−52.1 ppm, −53.7 ppm, −55.4 ppm
[8F, —OCF$_2$O—]
δ=−78.7 ppm, −80.6 ppm
[4F, —CF$_2$CH$_2$OCOCF$_3$]
δ=−76.7 ppm
[6F, —CF$_2$CH$_2$OCOCF$_3$]
δ=−89.1 ppm, −90.7 ppm
[16.4F, —OCF$_2$CF$_2$O—]
za=4.10, ya=4.18

Reference Example 1

Preparation of a mixture (Mixture 3) of CF$_3$CF$_2$O(CF$_2$CF$_2$CF$_2$O)$_{za}$CF$_2$CF$_2$CH$_2$OH (Compound 9), HOCH$_2$CF$_2$CF$_2$O(CF$_2$CF$_2$CF$_2$O)$_{za}$CF$_2$CF$_2$CH$_2$OH (Compound 10) and CF$_3$CF$_2$CF$_2$O(CF$_2$CF$_2$CF$_2$O)$_{za}$CF$_2$CF$_2$CF$_3$ (Compound 11)

In an argon atmosphere, 10 ml of dehydrated THF is mixed with 0.6 g of LiAlH$_4$ and ice-cooled. To a mixture was added dropwise a solution of 3 g of Mixture 1 (1045 in number average molecular weight) obtained in Example 2 dissolved in HFE-7100. After the addition, the mixture was stirred for one night at room temperature. To the mixture was added methanol and excess of LiAlH$_4$ was deactivated, then washed with acid and washed with water. The mixture was dried over dehydrating agent, and the agent was filtered off. The filtrate was concentrated to give 2.4 g of Mixture 3 containing Compound 9, Compound 10 and Compound 11.

Mixture 3 was a light yellow transparent liquid and 1.65 g/cm$^3$ in density at 20° C. Mixture 3 was identified by NMR with the result shown. Mixture 3 was 981 in number average molecular weight. $^{19}$F-NMR (solvent: none, reference material: OCF$_2$CF$_2$CF$_2$O in the obtained product being taken as −129.7 ppm)

δ=−129.7 ppm
[8F, —OCF$_2$CF$_2$CF$_2$O—]
δ=−83.7 ppm
[16F, —OCF$_2$CF$_2$CF$_2$O—]
δ=−86.4 ppm
[2F, —OCF$_2$CF$_2$CH$_2$OH]
δ=−127.5 ppm
[2F, —OCF$_2$CF$_2$CH$_2$OH]
δ=−130.7 ppm
[2F, CF$_3$CF$_2$CF$_2$O—]
δ=−84.7 ppm
[2F, CF$_3$CF$_2$CF$_2$O—]
δ=−82.4 ppm
[3F, CF$_3$CF$_2$CF$_2$O—]
za=4.01

$^1$H-NMR (solvent: none, reference material: D$_2$O)
δ=4.0 ppm
[2H, —OCF$_2$CF$_2$CH$_2$OH]
δ=4.3 ppm
[1H, —OCF$_2$CF$_2$CH$_2$OH]

INDUSTRIAL APPLICABILITY

In the present invention, it is possible to prepare a fluoropolyether having a molecular weight lower than a starting fluoropolyether and containing an acid fluoride by modifying a hydroxyl group of the starting fluoropolyether to a triflate or trifluoroacetate and cleaving the fluoropolyether with heating in the presence of a Lewis acid.

The invention claimed is:

1. A process for preparing a low-molecular weight fluoropolyether containing an acid fluoride by decomposing a triflate or trifluoroacetate of a fluoropolyether having a hydroxyl group in the presence of a Lewis acid.

2. The process as defined in claim 1, wherein the fluoropolyether having a hydroxyl group is one having a recurring unit of —(CF$_2$CF$_2$O)x(CF$_2$O)y-, and x and y are a real number of 1 to 100.

3. The process as defined in claim 1, wherein the fluoropolyether having a hydroxyl group is one having a recurring unit of —(CF$_2$CF$_2$CF$_2$O)z-, and z is a real number of 1 to 100.

4. The process as defined in claim 1, wherein the fluoropolyether having a hydroxyl group is one having a recurring unit of —(CF$_2$CF$_2$CF$_2$CF$_2$O)n-, and n is a real number of 1 to 100.

5. The process as defined in claim 1, wherein the triflate is at least one selected from the group consisting of
A-(CF$_2$CF$_2$O)x(CF$_2$O)yCF$_2$CH$_2$OTf,
TfOCH$_2$CF$_2$O(CF$_2$CF$_2$O)x(CF$_2$O)yCF$_2$CH$_2$OTf,
A-(CF$_2$CF$_2$CF$_2$O)zCF$_2$CF$_2$CH$_2$OTf,
TfOCH$_2$CF$_2$CF$_2$O(CF$_2$CF$_2$CF$_2$O)zCF$_2$CF$_2$CH$_2$OTf,
A-(CF$_2$CF$_2$CF$_2$CF$_2$O)nCF$_2$CF$_2$CF$_2$CH$_2$OTf, and
TfOCH$_2$CF$_2$CF$_2$CF$_2$O(CF$_2$CF$_2$CF$_2$CF$_2$O)nCF$_2$CF$_2$CF$_2$CH$_2$OTf,
wherein A is fluoroalkoxy, Tf is CF$_3$SO$_2$, and x, y, z and n are a real number of 1 to 100.

6. The process as defined in claim 1, wherein the trifluoroacetate is at least one selected from the group consisting of
A-(CF$_2$CF$_2$O)x(CF$_2$O)yCF$_2$CH$_2$OTfa,
TfaOCH$_2$CF$_2$O(CF$_2$CF$_2$O)x(CF$_2$O)yCF$_2$CH$_2$OTfa,
A-(CF$_2$CF$_2$CF$_2$O)zCF$_2$CF$_2$CH$_2$OTfa,
TfaOCH$_2$CF$_2$CF$_2$O(CF$_2$CF$_2$CF$_2$O)zCF$_2$CF$_2$CH$_2$OTfa,
A-(CF$_2$CF$_2$CF$_2$CF$_2$O)nCF$_2$CF$_2$CF$_2$CH$_2$OTfa, and
TfaOCH$_2$CF$_2$CF$_2$CF$_2$O(CF$_2$CF$_2$CF$_2$CF$_2$O)nCF$_2$CF$_2$CF$_2$CH$_2$OTfa,
wherein A is fluoroalkoxy, Tfa is CF$_3$CO, and x, y, z and n are a real number of 1 to 100.

7. The process as defined in claim 1, wherein the acid fluoride is at least one selected from the group consisting of
A-(CF$_2$CF$_2$O)xa(CF$_2$O)ya-CF$_2$COF,
FOC—CF$_2$O(CF$_2$CF$_2$O)xa(CF$_2$O)ya-CF$_2$COF,
A-(CF$_2$CF$_2$CF$_2$O)za-CF$_2$CF$_2$COF,
FOC—CF$_2$CF$_2$O(CF$_2$CF$_2$CF$_2$O)za-CF$_2$CF$_2$COF,
A-(CF$_2$CF$_2$CF$_2$CF$_2$O)na-CF$_2$CF$_2$CF$_2$COF, and
FOC—CF$_2$CF$_2$CF$_2$O(CF$_2$CF$_2$CF$_2$CF$_2$O)na-CF$_2$CF$_2$CF$_2$COF,
wherein A is fluoroalkoxy, 0.1x≤xa≤0.9x, 0.1y≤ya≤0.9y, 0.1z≤za≤0.9z, 0.1n≤na≤0.9n, and x, y, z and n are a real number of 1 to 100.

8. The process as defined in claim 2, wherein x and y are each a real number of 1 to 30, z is a real number of 1 to 30, and n is a real number of 1 to 30.

9. The process as defined in claim 1, wherein the acid fluoride is at least one selected from the group consisting of
A-(CF$_2$CF$_2$O)xa(CF$_2$O)ya-CF$_2$COF,
FOC—CF$_2$O(CF$_2$CF$_2$O)xa(CF$_2$O)ya-CF$_2$COF,
A-(CF$_2$CF$_2$CF$_2$O)za-CF$_2$CF$_2$COF,
FOC—CF$_2$CF$_2$O(CF$_2$CF$_2$CF$_2$O)za-CF$_2$CF$_2$COF,
A-(CF$_2$CF$_2$CF$_2$CF$_2$O)na-CF$_2$CF$_2$CF$_2$COF, and
FOC—CF$_2$CF$_2$CF$_2$O(CF$_2$CF$_2$CF$_2$CF$_2$O)na-CF$_2$CF$_2$CF$_2$COF, and the low-molecular weight fluoropolyether is at least one selected from the group consisting of A-($CF_2CF_2O$)xa($CF_2O$)ya-B,
A-($CF_2CF_2CF_2O$)za-B, and
A-($CF_2CF_2CF_2CF_2O$)na-B,
wherein A is fluoroalkoxy, B is fluoroalkyl, $0.1x \leq xa \leq 0.9x$, $0.1y \leq ya \leq 0.9y$, $0.1z \leq za \leq 0.9z$, and $0.1n \leq na \leq 0.9n$.

10. The process as defined in claim 1, wherein the triflate is at least one selected from the group consisting of A-($CF_2CF_2O$)x($CF_2O$)y$CF_2CH_2$OTf,
TfOCH$_2CF_2O$($CF_2CF_2O$)x($CF_2O$)y$CF_2CH_2$OTf,
A-($CF_2CF_2CF_2O$)z$CF_2CF_2CH_2$OTf,
TfOCH$_2CF_2CF_2O$($CF_2CF_2CF_2O$)z$CF_2CF_2CH_2$OTf,
A-($CF_2CF_2CF_2CF_2O$)n$CF_2CF_2CF_2CH_2$OTf, and
TfOCH$_2CF_2CF_2CF_2O$($CF_2CF_2CF_2CF_2O$)
n$CF_2CF_2CF_2CH_2$OTf, the acid fluoride is at least one selected from the group consisting of A-($CF_2CF_2O$)xa($CF_2O$)ya-$CF_2$COF,
FOC—$CF_2O$($CF_2CF_2O$)xa($CF_2O$)ya-$CF_2$COF,
A-($CF_2CF_2CF_2O$)za-$CF_2CF_2$COF,
FOC—$CF_2CF_2O$($CF_2CF_2CF_2O$)za-$CF_2CF_2$COF,
A-($CF_2CF_2CF_2CF_2O$)na-$CF_2CF_2CF_2$COF, and
FOC—$CF_2CF_2CF_2O$($CF_2CF_2CF_2CF_2O$)na-$CF_2CF_2CF_2$COF, and the low-molecular weight fluoropolyether is at least one selected from the group consisting of A-($CF_2CF_2O$)xa($CF_2O$)ya-B,
A-($CF_2CF_2CF_2O$)za-B, and
A-($CF_2CF_2CF_2CF_2O$)na-B,
wherein A is fluoroalkoxy, B is fluoroalkyl, Tf is $CF_3SO_2$, x, y, z and n are a real number of 1 to 100, $0.1x \leq xa \leq 0.9x$, $0.1y \leq ya \leq 0.9y$, $0.1z \leq za \leq 0.9z$, and $0.1n \leq na \leq 0.9n$.

11. The process as defined in claim 1, wherein the trifluoroacetate is at least one selected from the group consisting of A-($CF_2CF_2O$)x($CF_2O$)y$CF_2CH_2$OTfa,
TfaOCH$_2CF_2O$($CF_2CF_2O$)x($CF_2O$)y$CF_2CH_2$OTfa,
A-($CF_2CF_2CF_2O$)z$CF_2CF_2CH_2$OTf,
TfaOCH$_2CF_2CF_2O$($CF_2CF_2CF_2O$)z$CF_2CF_2CH_2$OTfa,
A-($CF_2CF_2CF_2CF_2O$)n$CF_2CF_2CF_2CH_2$OTfa, and
TfaOCH$_2CF_2CF_2CF_2O$($CF_2CF_2CF_2CF_2O$)
n$CF_2CF_2CF_2CH_2$OTfa, the acid fluoride is at least one selected from the group consisting of A-($CF_2CF_2O$)xa($CF_2O$)ya-$CF_2$COF,
FOC—$CF_2O$($CF_2CF_2O$)xa($CF_2O$)ya-$CF_2$COF,
A-($CF_2CF_2CF_2O$)za-$CF_2CF_2$COF,
FOC—$CF_2CF_2O$($CF_2CF_2CF_2O$)za-$CF_2CF_2$COF,
A-($CF_2CF_2CF_2CF_2O$)na-$CF_2CF_2CF_2$COF, and
FOC—$CF_2CF_2CF_2O$($CF_2CF_2CF_2CF_2O$)na-$CF_2CF_2CF_2$COF, and the low-molecular weight fluoropolyether is at least one selected from the group consisting of A-($CF_2CF_2O$)xa($CF_2O$)ya-B,
A-($CF_2CF_2CF_2O$)za-B, and
A-($CF_2CF_2CF_2CF_2O$)na-B,
wherein A is fluoroalkoxy, B is fluoroalkyl, Tfa is $CF_3CO$, x, y, z and n are a real number of 1 to 100, $0.1x \leq xa \leq 0.9x$, $0.1y \leq ya \leq 0.9y$, $0.1z \leq za \leq 0.9z$, and $0.1n \leq na \leq 0.9n$.

* * * * *